(12) United States Patent
Feygin et al.

(10) Patent No.: US 6,315,957 B1
(45) Date of Patent: Nov. 13, 2001

(54) ARTICLE COMPRISING A FILTER POCKET-PLATE

(75) Inventors: Ilya Feygin, Mountainside; Edward Theodore Heebner, Jr., Skillman, both of NJ (US)

(73) Assignee: Pharmacopeia, Inc., Princeton, NJ (US)

( * ) Notice: Subject to any disclaimer, the term of this patent is extended or adjusted under 35 U.S.C. 154(b) by 0 days.

(21) Appl. No.: 09/232,774

(22) Filed: Jan. 15, 1999

(51) Int. Cl.$^7$ ...................................................... B01L 11/00
(52) U.S. Cl. .......................... 422/101; 422/99; 422/102; 422/104; 435/287; 435/292; 435/293; 435/299; 435/300; 435/301; 436/178
(58) Field of Search ...................... 422/99–104; 435/287, 435/292, 293, 299, 300, 301; 436/174, 177, 178

(56) References Cited

U.S. PATENT DOCUMENTS

| | | | |
|---|---|---|---|
| 4,427,415 | * | 1/1984 | Cleveland ............................ 436/57 |
| 4,631,211 | | 12/1986 | Houghten . |
| 4,895,706 | * | 1/1990 | Root et al. ........................... 422/102 |
| 4,948,564 | * | 8/1990 | Root et al. ........................... 422/101 |
| 5,039,493 | * | 8/1991 | Oprandy ............................... 422/101 |
| 5,116,496 | * | 5/1992 | Scott .................................... 210/232 |
| 5,141,719 | * | 8/1992 | Fernwood et al. ................... 422/101 |
| 5,223,133 | * | 6/1993 | Clark et al. .......................... 210/232 |
| 5,227,137 | * | 7/1993 | Monti et al. .......................... 422/101 |
| 5,741,462 | * | 4/1998 | Nova et al. ........................... 422/68.1 |
| 5,925,732 | * | 7/1999 | Ecker et al. .......................... 530/334 |
| 5,939,024 | * | 8/1999 | Robertson ............................. 422/101 |
| 5,961,926 | * | 10/1999 | Kolb et al. ............................ 422/101 |
| 6,103,199 | * | 8/2000 | Bjornson et al. ..................... 422/100 |
| 6,117,397 | * | 9/2000 | Antonenko et al. .................. 422/101 |
| 6,159,368 | * | 12/2000 | Moring et al. ................... 210/321.75 |

* cited by examiner

*Primary Examiner*—Jill Warden
*Assistant Examiner*—Dwayne K. Handy
(74) *Attorney, Agent, or Firm*—DeMont & Breyer, LLC; Wayne S. Breyer; Jason Paul DeMont

(57) ABSTRACT

In some embodiments, the present invention provides a method and an article for segregating solid support media or other solids, from liquid, while at the same time maintaining such solids and liquid in intimate contact as may be required for various processing or chemical operations. In an illustrative embodiment, the present article comprises a filter pocket plate consisting of a plate with a plurality holes. A foraminous material projects through each hole in the plate such that a "pocket" is formed within each hole. In use, the aforedescribed filter pocket plate engages a vessel having one or more wells suitable for retaining liquid and for receiving the filter pockets. The filter pockets contain a solid material that is to be exposed to the liquid in the well. After exposure is complete, the solid material is readily removed from the liquid by simply disengaging the filter pocket plate, which retains the solid support media, from the vessel, which retains the liquid. In some embodiments, the present invention includes disengagement means for automatically removing the filter pocket plate from a cooperating vessel.

14 Claims, 3 Drawing Sheets ized opening 110 (i.e., about 200 microns) depends from lower end 104.

ARTICLE COMPRISING A FILTER POCKET-PLATE

FIELD OF THE INVENTION

The present invention relates to a device that is particularly useful for separating a solid support from a liquid.

BACKGROUND OF THE INVENTION

Filter bottom microtiter plates are widely used in conjunction with various synthesis, production and analytical processes. An illustrative filter bottom microtiter plate 100 depicted in FIG. 1 includes a plurality of "bottomless" wells 102, one of which is shown. A filter 106 is disposed within each well 102 near a lower end 104. A flexible seal 108 having a capillary-sized opening 110 (i.e., about 200 microns) depends from lower end 104.

When filter bottom microtiter plate 100 is stationary or static, the filter 106/flexible seal 108 within each well 102 is capable of retaining both a resin 112, such as a 50–1000 micron solid support as is often used for solid-phase synthesis, and a liquid 114. Under acceleration, such as when filter bottom microtiter plate 100 is centrifuged, filter 106/flexible seal 108 pass liquid 114 but retain resin 112.

Filter bottom microtiter plates have been used in conjunction with solid-phase synthesis methods. Solid-phase synthesis involves linking a first chemical "base structure" molecule to a solid support media and subsequently adding, seriatim, chemical building blocks, or, alternatively, effecting chemical structural changes to the base structure (e.g., ring opening or closing). The base structure molecule participates in one or more reaction steps with the added chemical building blocks. Chemical compounds derived from the base structure molecule are thereby generated.

Each chemical compound, and its base structure molecule precursor, is typically attached to the solid support media via a cleavable linker that covalently links the chemical compound to the support media. For assay purposes, the various chemical compounds are usually removed from the support media. Such removal is accomplished by cleaving the linker, such as by exposure to long-wave ultraviolet light. The cleaved chemical compounds are typically eluted into a solvent that is recovered.

The elution operation may be carried out in wells 102 of filter bottom microtiter plate 100. To separate liquid 114 (e.g., solvent) from the solid support media 112, plate 100 is accelerated, such as by centrifuging. Such acceleration drives liquid 114 through filter 106/flexible seal 108. The solid support media is retained by the filter.

While filter bottom microtiter plate 100 provides satisfactory performance, it has a relatively complex structure. Such complexity is reflected in the cost of such plate, which can reach $10.00 per plate. The art would thus benefit from a simpler filter plate design that is less costly to implement.

SUMMARY OF THE INVENTION

In one embodiment, the present invention provides a method and an article for segregating solid support media or other solids, from liquid, while at the same time maintaining such solids and liquid in intimate contact as may be required for various processing or chemical operations.

In an illustrative embodiment in accordance with the present teachings, such an article comprises a plate having a plurality of holes. A mesh-like or foraminous material projects through each hole such that a "pocket," akin to a pocket of a billiards table, is formed within each hole. Each of such pockets (hereinafter "filter pockets") comprises an amount of mesh suitable for retaining a small quantity of solid material.

In use, the aforedescribed plate/filter pockets (hereinafter "filter pocket plate") engages a vessel having one or more wells suitable for retaining liquid and for receiving the filter pockets of the filter pocket plate. In one embodiment, the filter pockets are advantageously arrayed in a standard pattern that complements the location of wells in a standard multi-well plate so that the filter pocket plate can be used therewith. The filter pockets contain a solid material that is to be exposed to the liquid in the well. After exposure, the solid material is readily removed from the liquid by simply disengaging the filter pocket plate, which retains the solid support media, from the vessel, which retains the liquid.

In an illustrative application, the filter pocket plate provides a means for solid phase synthesis. In such an application, a filter pocket plate is engaged to a multi-well plate. The filter pockets receive solid support media useful for solid phase synthesis. The mesh comprising the filter pockets is suitably selected to retain the solid support media. Liquid comprising one or more chemical building blocks for reacting with a reactive functionality on the solid support media, or comprising a solvent for eluting a compound that has resulted from such a reaction, is in intimate contact with the solid support media. Such liquid typically passes freely between the filter pocket and the surrounding well.

At various stages during synthesis, or after synthesis is completed, it may be desirable to separate the solid support media from the liquid. This can be done by manually disengaging the filter pocket plate, which retains the solid support media, from the multi-well plate. As desired, the filter pocket plate can be readily re-engaged to the multi-well plate to effect further contact between the solid support media and the liquid. Moreover, once the filter pocket plate is disengaged from the multi-well plate, it can be engaged to additional multi-well plates for exposure different liquids.

In a further embodiment, which is useful for both the illustrative solid-phase synthesis application or other applications, the present invention further includes disengagement means for "automatically" separating the filter pocket plate from an engaged vessel. The disengagement means are advantageously actuated via an accelerative force, such as may be provided by a centrifuge.

In one embodiment, the disengagement means comprises two arms that are rotatably supported at a fulcrum providing a "scissors-type" lifting mechanism. Upper ends of the arms abut and underlie a portion of a filter pocket plate that is engaged to a vessel. Under acceleration, the arms rotate in opposite directions about the fulcrum, whereby the upper ends of the arms "rise" (i.e., the "scissors" close). As the upper ends of the arms rise, the overlying filter pocket plate is lifted off of the cooperating vessel. A locking means prevents the disengaging means from returning the filter pocket plate to the vessel when acceleration is reduced.

The present filter pocket plate is disposable and far less expensive than conventional filter bottom microtiter plates.

DETAILED DESCRIPTION

Figure 1:
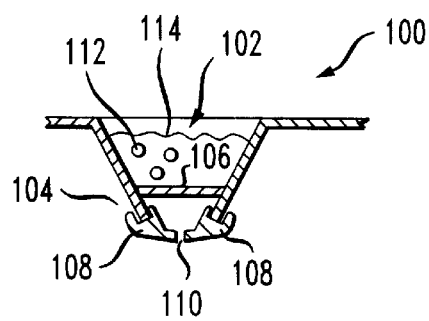
FIG. 1 depicts a conventional filter bottom microtiter plate.
Figure 2:
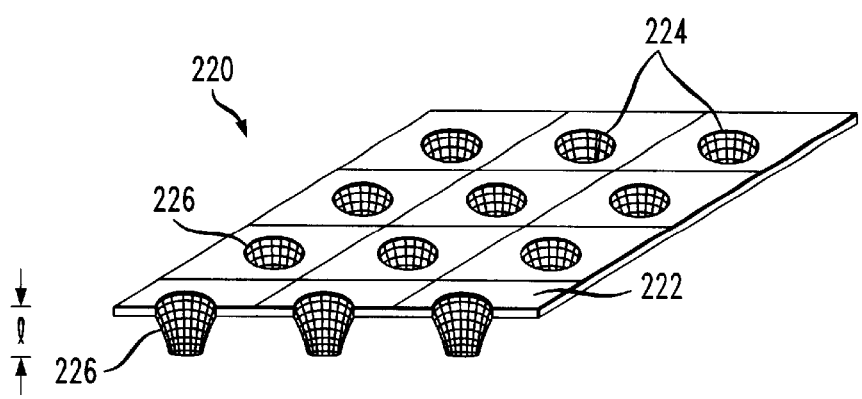
FIG. 2 depicts a filter pocket plate in accordance with an illustrative embodiment of the present invention.

FIG. 2 depicts filter pocket plate 220 in accordance with the present teachings. Filter pocket plate 220 includes card or plate 222 having a plurality of holes 224 defined therein. A foraminous or mesh-like material (hereinafter "mesh") projects a distance l through each hole 224 forming filter pockets 226. Each filter pocket 226 is long enough to retain a desired quantity of solid support media or other particles. A pocket length (i.e., the distance l), of about 0.25 inches is expected to retain a sufficient amount of support media for most applications.

Foramina in the mesh comprising filter pockets 226 are suitably sized for retaining a particular solid material. For example, solid supports such as are typically used for solid-phase synthesis have a diameter in the range of about 50 to 1000 microns. For such an application, the mesh advantageously has foramina in the range of about 40–50 microns. It will be appreciated, however, that if a specific solid support is exclusively used, the foramina can be suitably sized for the nominal diameter of that solid support (allowing for an expected variation in nominal diameter) and for efficient exchange of fluid through the mesh.

In use, filter pocket plate 220 engages a vessel that is suitable for retaining a quantity of liquid that is intended to contact solid support media or other solids retained in each filter pocket 226. The liquid can be various reagents, solvents or the like. If the material in any given filter pocket 226 is to be exposed to a different liquid than the material in other filter pockets within filter pocket plate 220, then individual reservoirs or wells should be provided within the vessel for retaining such different liquids. If all the solid material within the filter pockets of a filter pocket plate are to be exposed to the same liquid, then a vessel having a single well or reservoir is sufficient.

Figure 3:
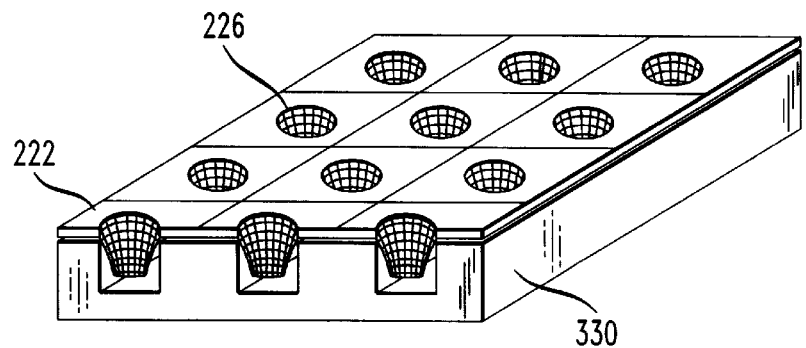
FIG. 3 depicts the filter pocket plate of FIG. 2 engaged with a standard multi-well plate.

Holes 224 in plate 222 are advantageously disposed in a standard pattern or array that complements a standard multi-well plate. For example, in one embodiment, a filter pocket plate has 96 holes (and 96 filter pockets) that are arranged in an 8×12 array. Each hole has a diameter of approximately 0.2 inches. Pocket length l is approximately 0.25 inches. Such dimensions allow filter pocket plate 200 to be used in conjunction with a standard 96-well shallow-well plate. FIG. 3 depicts filter pocket plate 220 of FIG. 2 engaged with a standard shallow-well plate 330.

The present filter pocket plate can be fabricated using a variety of methods. In one embodiment, card 222 is pre-drilled to provide an array of holes 224, and then prefabricated filter pockets are inserted into each hole. In another embodiment, card 222 is predrilled to provide an array of holes, and then mesh is laid over card 222 and forced into each of the holes 224 in the card. After the pockets are created, the mesh is welded, melted or glued to card 222. In a third embodiment, there is no card, per se; rather, a piece of mesh is stamped to provided pockets and then subsequently reinforced, such as with metal ribs or rods. Card 222 and filter pockets 226 are advantageously comprised of polypropylene, although other materials may suitably be used as a function of the prevailing chemical environment, cost considerations or other factors.

Figure 4:
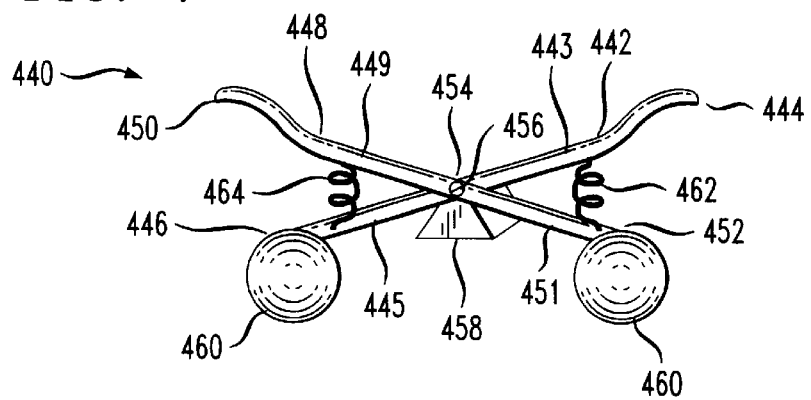
FIG. 4 depicts disengaging means for automatically disengaging the present filter pocket plate from a standard multi-well plate.

After a suitable contact period between the solid media and the surrounding liquid, it is typically desirable to disengage filter pocket plate 220 from the engaged vessel for storage, etc. Such disengagement can be manually performed; however, liquid tends to be retained within the foramina of the mesh, in the solid support material (depending upon pore size) and in the interstices between individual solid support particles due to capillary action. In some embodiments, disengagement occurs automatically and is advantageously effected in a manner that substantially avoids such retained liquid. An illustrative embodiment of disengagement means suitable for automatic disengagement is depicted in FIG. 4.

Illustrative disengagement means 440 includes first and second arms 442, 448 that are rotatably supported in a scissors-type configuration at a fulcrum 454. In one embodiment, the rotatable support is provided by a pivot pin 456 that passes through a central region of each arm 442, 448. Pivot pin 456 depends from an arm support 458.

Fulcrum 454 functionally divides first arm 442 into first portion 443 and second portion 445. Likewise, the fulcrum functionally divides second arm 448 into first portion 449 and second portion 451. A region of first portion 443 of first arm 442 that is distal to fulcrum 454 and proximal to first end 444 advantageously has a substantially arcuate shape. Similarly, a region of first portion 449 of second arm 448 that is distal to fulcrum 454 and proximal to first end 450 advantageously has a substantially arcuate shape.

A mass 460 depends from the second portion of scissored arms 442, 448 near a respective second end 446, 452 thereof. Resilient member 462 links first portion 443 of first arm 442 to second portion 451 of second arm 448 on one side (e.g., the right side) of fulcrum 456, and resilient member 464 links first portion 449 of second arm 448 to second portion 445 of first arm 442 on the other side of the fulcrum.

Due to the scissors-type configuration of arms 442, 448, masses 460 disposed at the second end of each arm, in conjunction with gravity, each provide a force (i.e., weight) that tends to drive the linked first and second portions of the arms in opposite directions. As a result, resilient members 462, 464 are placed in tension. When the disengagement means is static (i.e., not accelerated), the compressive force of resilient members 462, 464 overcomes the weight of masses 460 such that arms 442, 448 are maintained in an "open" configuration.

Figure 5:
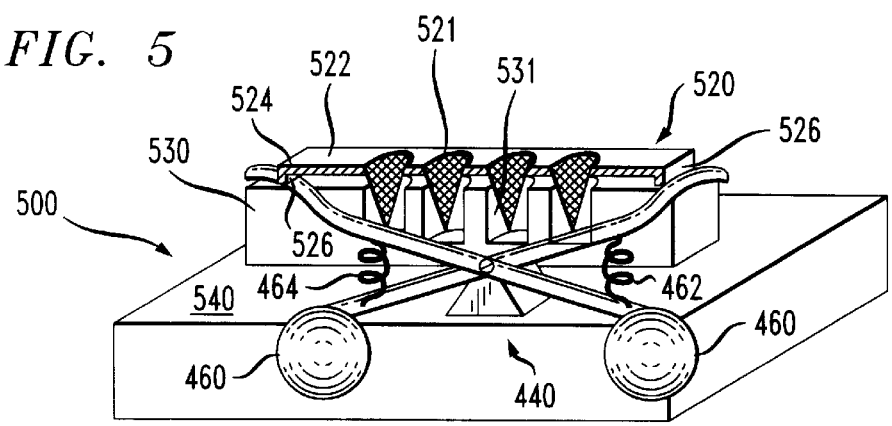
FIG. 5 depicts the disengaging means of FIG. 4 operatively engaged to the present filter pocket plate for removal from a multi-well plate.

FIG. 5 depicts arrangement 500 that facilitates operative engagement between disengaging means 440 and a filter pocket plate. Arrangement 500 comprises disengaging means 440 disposed on a support 540. Support 540 is appropriately sized and advantageously adapted for receiving a vessel, such as multi-well plate 530. Such adaptations include alignment and hold-down features. Moreover, support 540 is physically adapted, as required, to be received by a centrifuge or other means capable of accelerating arrangement 500.

As depicted in FIG. 5, arrangement 500 receives filter pocket plate 520 that is disposed on multi-well plate 530. Filter pocket plate 520 and multi-well plate 530 are shown in partial section for clarity of illustration. Filter pockets 521 are shown received by wells 531 of the multi-well plate.

Filter pocket plate 520 is advantageously physically adapted to operatively engage disengagement means 440. In the illustrated embodiment, the physical adaptation comprises a portion 524 of card 522 that overhangs multi-well plate 530. Overhanging portion 524 advantageously includes locking means, realized in the illustrated embodiment as a downwardly-extending lip 526 located at the perimeter of card 522.

In the embodiment depicted in FIG. 5, multi-well plate 530 is received at a location on support 540 such that the arcuate portion of arms 442, 444 underlie and abut overhanging portion 524 of card 522. Such abutment provides the operative engagement required for disengagement means 440 to disengage filter pocket plate 520 from multi-well plate 530, as described below.

Figure 6:
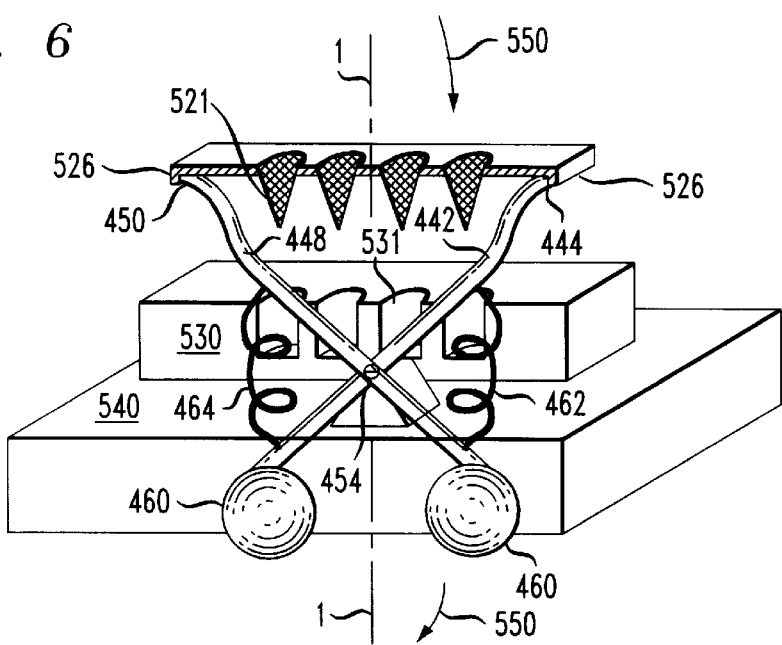
FIG. 6 depicts the arrangement of FIG. 5 after the disengaging means has disengaged the filter pocket plate from the multi-well plate.

FIG. 5 depicts arrangement 500, filter pocket plate 520 and multi-well plate 530 before acceleration. FIG. 6 depicts the same elements under acceleration moving in circular motion as indicated by direction vector 550. Such acceleration actuates disengagement means 440.

Under acceleration, the force of the accelerated masses 460 is sufficient to overcome the compressive force of resilient members 462, 464. The masses 460 move towards axis 1—1, which is directed tangentially to the circular motion and runs through fulcrum 454. Such movement causes the linked first and second portions of the arms to rotate away from one another. Such rotation causes the scissored arms to close on one another (in the manner of a scissors). As that occurs, filter pocket plate 520 is lifted off of the multi-well plate 530.

In addition to providing an actuating force for disengagement means 440, accelerating filter pocket plate 520 reduces the likelihood that liquid will be retained in the foramina of the mesh, in the solid support material or in the interstices between solid support material.

Locking means prevents arms 442, 448 from dropping towards support 540 when the rotational velocity is reduced such that the force generated due to acceleration is insufficient to overcome the compressive force exerted by resilient members 462, 464. In such a manner, the locking means prevents filter pocket plate 520 from re-engaging multi-well plate 530.

As previously described, locking means is realized in the illustrated embodiment as downwardly-extending lip 526. At a threshold rotational velocity, first ends 444, 450 of the arms pass underneath lip 526, as is depicted in FIG. 6. The threshold velocity is primarily a function of masses 460 and the "spring constant" of resilient members 462, 464. Once the ends of arms 442, 448 pass under lip 526, they are prevented from dropping back towards support 540. The arcuate shape of first end 444, 450 of respective arms 442, 444 facilitates such locking engagement.

Figure 7:
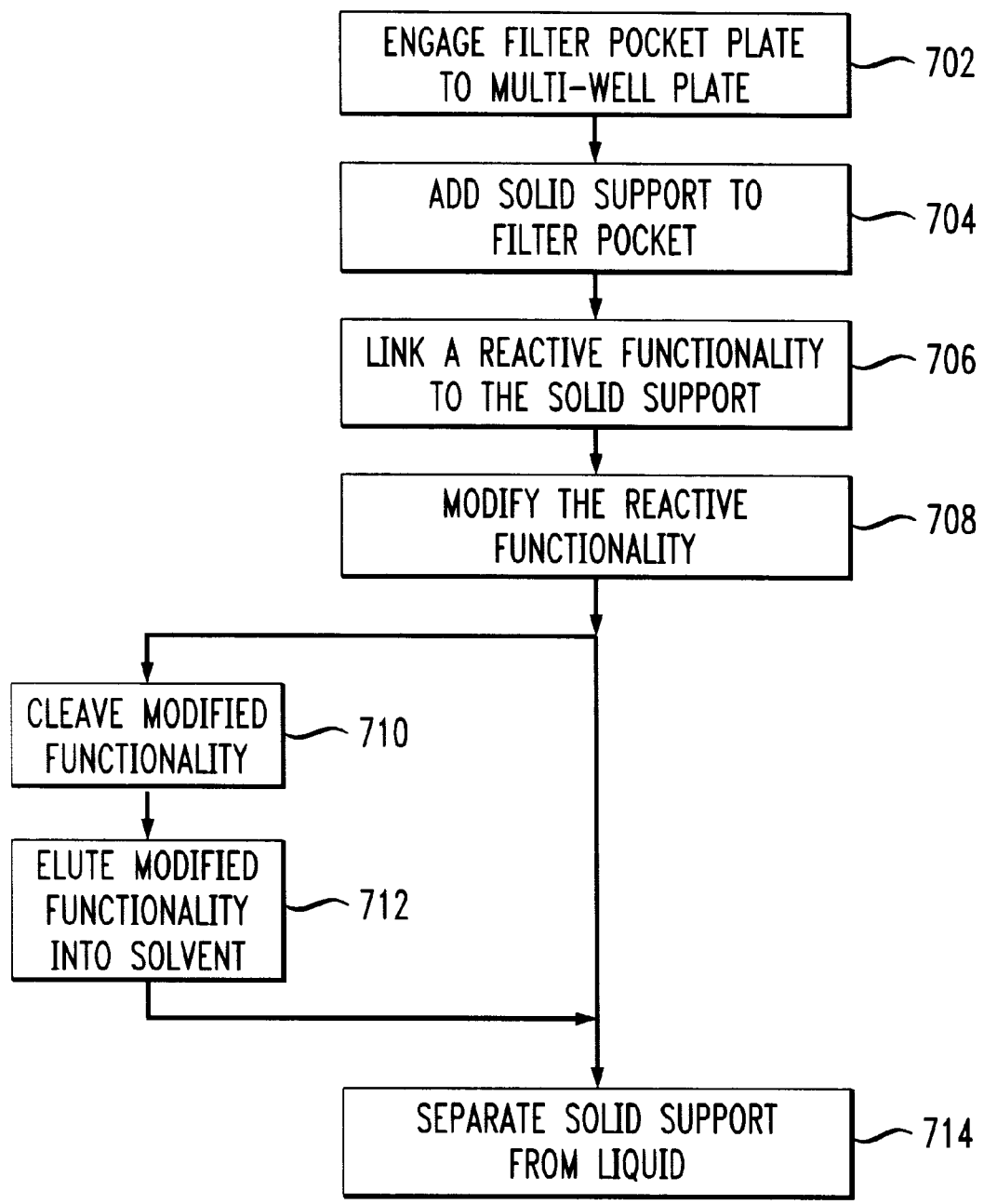
FIG. 7 depicts a flow chart of a method for solid-phase synthesis in accordance with an illustrative embodiment of the present invention.

The present filter pocket plate can be used for a variety of applications. For example, in one embodiment in accordance with the present invention, the filter pocket plate provides a method and apparatus for carrying out solid-phase synthesis. Such an apparatus is described with reference to FIG. 5, and the method is depicted by flow diagram in FIG. 7. For background, a process of combinatorial solid-phase synthesis is described in U.S. Pat. No. 5,721,099, incorporated by reference herein.

In the presently described illustrative application, filter pocket plate 520 is engaged to conventional multi-well plate 530, as per operation block 702. Filter pockets 521 receive an amount of solid support media, as indicated in operation 704. As part of the solid-phase synthesis, the solid support media are covalently-linked to a reactive functionality which provides a base structure from which a plurality of chemical compounds are synthesized, per operation 706.

According to operation 708, the base structure is modified in a series of steps that may include the sequential addition of various reactive moieties, and/or may include causing chemical structural changes to the base structure (e.g., ring opening or closing). In that manner, a variety of chemical compounds are synthesized.

Solid support media useful for solid-phase synthesis include, without limitation, cellulose beads, controlled pore-glass beads, silica gels, polystyrene beads optionally cross linked with divinylbenzene and optionally grafted with polyethylene glycol and optionally functionalized with amino, hydroxy, carboxy, or halo groups, grafted copoly beads, polyacrylamide beads, latex beads, dimethylacrylamide beads optionally cross linked with N,N'-bis-acryloyl ethylene diamine, glass particles coated with hydrophobic polymer, and the like.

In one embodiment of a method in accordance with the present teachings, after modifying the reactive functionality to form a compound, the solid support is separated from a surrounding liquid, such as a liquid containing reactive moieties that participated in a reaction that formed the compound. In such an embodiment, operations 710 (i.e., cleaving the modified functionality) and 712 (i.e., elute modified functionality into solvent) are bypassed, and processing proceeds directly from operation 708 to operation 714, wherein the solid support is separated from liquid.

The separation operation 714 comprises disengaging filter pocket plate 520 from multi-well plate 530. Such disengagement can be accomplished either manually or automatically. Automatic removal is advantageously effected via the disengagement means previously described using, for example, a centrifuge. In such a manner, solid support media containing compounds synthesized via solid phase synthesis are separated from reagents or other liquid.

After filter pocket plate 520 is removed from the multi-well plate 530, it can be stored. Moreover, filter pocket plate 520 can be sectioned so that the resulting sections can be treated differently (e.g., a first section is stored, a second section is engaged to an additional multi-well plate to participate in further reactions, a third section is utilized in assays, etc.).

The reactive functionality (i.e., base structure) is typically attached to the solid support via a cleavable linker. After the reactive functionality is modified, the resulting compound is typically removed from the support for assay purposes, etc. Removal is typically accomplished by cleaving the linker, such as by exposure to long-wave ultraviolet light. The cleaved chemical compounds are then eluted into a solvent.

Thus, in a further embodiment, the present filter pocket plate can be used during the elution phase wherein synthesized compounds are cleaved from the solid support and eluted into a solvent, as per operations 710 and 712. After elution, the solid supports are separated from the solvent, per operation 714, as described above. The product-containing solvent remaining in the multi-well plate is then recovered. If desired, multiple separation (disengagement) steps whereby the solid supports are separated from solvent, then reintroduced into the solvent (either the "used" solvent or "fresh" solvent) can be performed.

The embodiments described in this specification are merely illustrative of the invention. Many variations may be devised by those skilled in the art without departing from the scope and spirit of the invention. For example, while in the aforedescribed illustrative embodiments the material comprising the filter pockets freely passes liquid, in other embodiments, such filter pockets are comprised of a material that is capable of retaining liquid. Liquid is removed from such filter pockets under acceleration. Thus, in such an embodiment, accelerative forces can be used to (1) drive liquid from the filter pockets, and (2) separate the filter pocket plate from a cooperating vessel using the disengagement means. It is therefore intended that such variations be included within the scope of the following claims and their equivalents.

We claim:

1. An article comprising a filter pocket plate for use in conjunction with a solid material, the filter pocket plate having:
 a plate including a plurality of holes; and
 a quantity of foraminous material integrally connected to and projecting through each hole, the projecting material defining a filter pocket, wherein the foraminous material is suitably selected to retain the solid material within the filter pocket.

2. The article of claim 1, further comprising the solid material, wherein the solid material is disposed within the filter pockets.

3. The article of claim 2, wherein the solid material is a solid support selected from the group consisting of cellulose beads, controlled pore-glass beads, silica gels, polystyrene beads optionally cross linked with divinylbenzene and optionally grafted with polyethylene glycol and optionally functionalized with amino, hydroxy, carboxy, or halo groups, grafted copoly beads, polyacrylamide beads, latex beads, dimethylacrylamide beads optionally cross linked with N,N'-bis-acryloyl ethylene diamine, glass particles coated with hydrophobic polymer, and the like.

4. The article of claim 3, wherein foramina of the foraminous material have a size within the range of about 40 microns to about 500 microns.

5. The article of claim 3, wherein a reactive functionality is covalently linked to the solid support.

6. The article of claim 1, and further comprising a vessel that engages the filter pocket plate, wherein the filter pockets are received by at least one well of the vessel.

7. The article of claim 6, wherein the vessel comprises a plurality of wells such that each filter pocket of the filter pocket plate is received by one of the wells.

8. The article of claim 7, further comprising the solid material, wherein the solid material is disposed within the filter pockets.

9. The article of claim 8, wherein the solid material is a solid support selected from the group consisting of cellulose beads, controlled pore-glass beads, silica gels, polystyrene beads optionally cross linked with divinylbenzene and optionally grafted with polyethylene glycol and optionally functionalized with amino, hydroxy, carboxy, or halo groups, grafted copoly beads, polyacrylamide beads, latex beads, dimethylacrylamide beads optionally cross linked with N,N'-bis-acryloyl ethylene diamine, glass particles coated with hydrophobic polymer, and the like.

10. The article of claim 6, and further comprising:
 a support that receives the engaged vessel and filter pocket plate; and
 disengagement means disposed on the support, wherein said disengagement means are operatively engaged to the filter pocket plate such that when actuated, the disengagement means are operable to disengage the filter pocket plate from the vessel.

11. The article of claim 10, wherein the disengagement means comprises:
 first and second arms that are rotatably supported at a fulcrum, the fulcrum dividing each arm into a first and a second part;
 first and second masses depending from the second part of each of the first and second arms;
 a first resilient member that mechanically links the first part of the first arm to the second part of the second arm; and
 a second resilient member that mechanically links the first part of the second arm to the second part of the first arm.

12. The article of claim 11, wherein when said disengagement means is operatively engaged to the filter pocket plate, the first part of the first and second arms abuts and underlies a portion of the filter pocket plate.

13. The article of claim 12, wherein the portion of the filter pocket plate further comprises locking means that prevents the filter pocket plate from re-engaging the vessel after it has been disengaged therefrom by the disengaging means.

14. The article of claim 13, wherein said locking means comprises a downwardly-extending lip.

* * * * *